US011471484B2

(12) United States Patent
Moussa et al.

(10) Patent No.: US 11,471,484 B2
(45) Date of Patent: Oct. 18, 2022

(54) FULLERENE AND ITS USE TO MAINTAIN GOOD HEALTH AND TO PROLONG THE EXPECTED LIFESPAN OF MAMMALS (71) Applicant: Fathi Moussa, Cachan (FR)

(72) Inventors: Fathi Moussa, Ben Arous (TN); Manef Abderrabba, Sidi Rezig-Megrine (TN)

(73) Assignee: Fathi Moussa, Cachan (FR)

( * ) Notice: Subject to any disclaimer, the term of this patent is extended or adjusted under 35 U.S.C. 154(b) by 133 days.

(21) Appl. No.: 15/927,703

(22) Filed: Mar. 21, 2018

(65) Prior Publication Data

US 2018/0271906 A1 Sep. 27, 2018

Related U.S. Application Data (63) Continuation of application No. 14/130,020, filed on Dec. 30, 2013, now abandoned.

(30) Foreign Application Priority Data

Jun. 30, 2011 (TN) .............................. TN2011/0327

(51) Int. Cl.
*A61K 33/44* (2006.01)
*A23L 33/10* (2016.01)
*A23D 9/007* (2006.01)
*A23D 7/005* (2006.01)
*A23L 3/358* (2006.01)

(52) U.S. Cl.
CPC ............ *A61K 33/44* (2013.01); *A23D 7/0053* (2013.01); *A23D 9/007* (2013.01); *A23L 3/358* (2013.01); *A23L 33/10* (2016.08)

(58) Field of Classification Search
CPC ......... A61K 33/44; A23L 33/10; A23L 3/358; A23D 7/0053; A23D 9/007
USPC ....................................................... 424/125
See application file for complete search history.

(56) References Cited

U.S. PATENT DOCUMENTS

| | | | |
|---|---|---|---|
| 5,994,410 | A | 11/1999 | Chang et al. |
| 6,844,429 | B2 | 1/2005 | Mikata et al. |
| 2002/0098180 | A1 | 7/2002 | Lei et al. |
| 2003/0162837 | A1 | 8/2003 | Dugan et al. |
| 2008/0206222 | A1 | 8/2008 | Miwa et al. |
| 2011/0003773 | A1 | 1/2011 | Kepley et al. |
| 2012/0171121 | A1 | 7/2012 | Webster |
| 2014/0140985 | A1 | 5/2014 | Moussa et al. |
| 2015/0258094 | A1 | 9/2015 | Chen et al. |

FOREIGN PATENT DOCUMENTS

| | | |
|---|---|---|
| CN | 103705388 A | 4/2014 |
| TN | 2009/000493 A | 6/2011 |
| UA | 102139 C2 | 6/2013 |
| WO | 2005105214 A1 | 11/2005 |
| WO | 2013025180 A1 | 2/2013 |

OTHER PUBLICATIONS

Chinese Office Action for Chinese Patent Application No. 201280037654.0, dated May 22, 2017 (11 pages).
European Office Action for European Patent Application No. 12780896.2, dated Dec. 9, 2016 (3 pages).
International Search Report for International Patent Application No. PCT/TN2012/000003, dated Dec. 18, 2012 (7 pages).
Written Opinion of the International Searching Authority for International Patent Application No. PCT/TN2012/000003, dated Dec. 18, 2012 (7 pages).
Agafonov et al., "Preparation of fullerene solution useful in production of cosmetics, drugs, biologically active compositions and nanotechnology comprises exposing fullerene in solvent to ultrasound," C2004-111690 (1 page).
Andrievsky et al., "Peculiarities of the Antioxidant and Radioprotective Effects of Hydrated C60 Fullerene Nanostructures in vitro and in vivo," Free Radical Biology & Medicine, Jun. 17, 2009, pp. 786-793, vol. 47.
Baati et al., "The prolongation of the lifespan of rats by repeated oral administration of [60] fullerne," Biomaterials, 2012, pp. 4936-4946, vol. 33.
Gharbi, et al., "[60] Fullerene is a Powerful Antioxidant in Vivo with No Acute or Subacute Toxicity," Nano Letters, 2005, pp. 2578-2585, vol. 5, No. 12.
Gianni et al., "Study of the Cytotoxic Effects of the New Synthetic Isothiocyanate CM9 and Its Fullerene Derivative on Human T-Leukemia Cells," Toxins, 2015, pp. 535-552, vol. 7.
Injac et al., "Protective Effects of Fullerenol C60(OH)24 Against Doxorubicin-Induced Cardiotoxicity and Hepatotoxicity in Rats with Colorectal Cancer," Biomaterials, 2009, pp. 1184-1196, vol. 30.
Petrovic et al., "Applications of Anti/Prooxidant Fullerenes in Nanomedicine Along with Fullerenes Influence on the Immune System," Journal of Nanomaterials, 2015, pp. 1-12, vol. 2015.
Unknown, "Cosmetic composition protecting from sunburn— contains fullerene(s), oil component, UV absorber, etc.," 1998 (1 page).

*Primary Examiner* — Adam C Milligan
(74) *Attorney, Agent, or Firm* — Barnes & Thornburg LLP; Ryan L. Marshall (57) ABSTRACT

A water-insoluble fullerene is at least partially dissolved in a biocompatible lipid carrier, especially a fat or an oil such as butter, olive oil, and liquid paraffin. When administered to mammals, the fullerene, most preferably [60]fullerene dissolved in olive oil, scavenges free radicals and prolongs life span in rats.

5 Claims, 5 Drawing Sheets

|  | Oral | IP |
|---|---|---|
|  | Value ± SD (CV %) | Value ± SD (CV %) |
| $t_{½}$ (h) | 9.3 ± 2.7 (28.5 %)ns | 13.9 ± 2.9 (20.8 %) |
| Cmax (µg/ml) | 0.52 ± 0.16 (30.7 %)** | 1.47 ± 0.15 (10.2 %) |
| Tmax (h) | 8.0 ± 0.1 | 4.0 ± 0.1 |
| $AUC_0^\infty$ (µg.h.ml⁻¹) | 4.37 ± 0.60 (0.14 %)*** | 21.21 ± 1.50 (7.1 %) |
| Cl/F (ml.h⁻¹) | 185.5 ± 27.5 (14.8 %)*** | 37.8 ± 2.6 (6.9 %) |
| Vd/F (L) | 2.56 ± 1.09 (42.6 %) | 0.75 ± 0.12 (15.5 %) |
| MRT (h) | 12.6 ± 0.9 (7.1 %)* | 18.0 ± 1.9 (10.6 %) |

Statistical differences were evaluated by T-test. *p<0.05, p<0.01, *p<0.001

FIG. 3

|  | Oral ($D_1$) | Oral ($D_7$) | i.p. ($D_1$) | i.p. ($D_7$) |
|---|---|---|---|---|
| WB (µg/ml) Mean (SD) | 0.03 (± 0.01) | 0.18 (± 0.06) | 0.36 (± 0.06) | 0.58 (± 0.17) |
| Liver (µg/g) Mean (SD) | 0.21 (± 0.04) | 2.92 (± 0.82) | 4.91 (± 1.52) | 31.19 (± 11.60) |
| Spleen (µg/g) Mean (SD) | 2.99 (± 1.37) | 51 (± 14) | 23 (± 6) | 191 (± 40) |
| Brain (µg/g) Mean (SD) | nd | 0.013 (± 0.003) | nd | 0.54 (± 0.17) |

FULLERENE AND ITS USE TO MAINTAIN GOOD HEALTH AND TO PROLONG THE EXPECTED LIFESPAN OF MAMMALS

This application claims benefit of Tunisian Provisional Application No. TN 2011/327 filed Jun. 30, 2011 the contents of which are incorporated herein by reference.

BACKGROUND OF THE INVENTION

1. Field of the Invention

The present invention concerns [60]fullerene and stable biocompatible compositions comprising [60]fullerene dissolved in a carrier. The present invention also relates to a method for increasing the expected lifespan (longevity) of a mammal, which comprises a step of administering [60]fullerene or a composition comprising a therapeutically effective amount of [60]fullerene. The present invention further concerns a method for preserving a mammal to damages caused by free radicals using said [60]fullerene or said composition.

2. Description of Related Art

Free radicals, such as oxygen radicals and other reactive oxygen/nitrogen/chlorine species (hydroxyl, nitric oxide radicals), are constantly formed in vivo. Some of these molecules are physiologically useful, but they can also result in pathological oxidative stress to cells and tissues. Endogenous defences include both antioxidants and repairing systems. However, excess production of free radicals, their production in inappropriate relative amounts or deficiencies in endogenous defences can have deleterious effects. Free radicals can cause oxidative damage to lipids, DNA, bio molecules, rises in the concentration of intracellular calcium, as well as activation of proteases, nucleases and protein kinases. Considerable evidence supports the view that oxidative damage involving free radicals occurs in most, if not all, human diseases. Oxidative stress is now recognized as an important contributor to the development of many human diseases including liver fibrosis, ischemia-reperfusion, atherosclerosis, neurodegenerative disease and age-related cancer as well as to process of ageing. Thus antioxidants and systems that can protect against oxidative stress are needed to maintain health. A large body of scientific evidence supports that oxidative stress is directly responsible for aging (Aging Cell. 2009, 8(3):258-69) and an array of neuropathology conditions (Nutrition 2010, 26:595-603. Neurochem Res. 2007, 32:757-73). The free radical theory of aging proposes that the organism is unable to repair all of them and that, with time, unrepaired damages accumulate and put the organism at risk: in other words, free radicals provoke aging and death (FEBS Letters 2009, 498: 183-186. J. Neurochem. 2009, 108:1251-65). Antioxidants are the substances able to react with free radicals and to protect the body from the damage caused by these molecules (Ital J Biochem. 2006, 55:263-282). In particular, consumption in excess of some foods which are rich sources of antioxidants is considered to promote good health and longevity. It is now believed that the maintenance of redox balance within the body can forestall aging and promote good health and longevity.

Due to its 30 carbon double bonds, [60]fullerene (Buckminsterfullerene, $C_{60}$) is a powerful free radical scavenger which characterize it as a radical sponge (Science 1991, 254, 1 83-1185). Biological applications of fullerenes and derivatives, in particular as antioxidants, have been extensively reviewed (Bioorg. Med. Chem. 1996, 4: 767-779. Eur. J. Med. Chem. 2003, 38: 913-923. Biomedicine & Pharmacotherapy, 2005, 59: 351-358). $C_{60}$ is only soluble in a limited number of organic solvents, such as toluene, benzene, chloronaphtalene and dichlorobenzene. Availability of biocompatible aqueous solutions of $C_{60}$ and its derivatives that are insoluble in water have been major obstacles to toxicity and in vivo studies of this new family of compounds. Biological properties of water-insoluble fullerenes are still misunderstood and to our knowledge there are no certified toxicology data about them. Most of the fullerenes studied until now are water-soluble derivatives, since study of water-insoluble fullerenes, such as pristine $C_{60}$, in biological medium proves difficult. It is a common practice to derivatize the fullerene core with substituants such as OH, COOH, NH2 to increase hydrophilicity (Bioorg. Med. Chem. 1996, 4: 767-779. Eur. J. Med. Chem. 2003, 38: 913-923. Biomedicine & Pharmacotherapy, 2005, 59: 351-358). Water-soluble $C_{60}$ derivatives have been found to retain in vitro the free radical scavenger properties of their parent fullerene molecule, allowing these properties to be exploited in biological systems. Many patents already exist for a broad range of biomedical applications and other commercial applications of water-soluble fullerenes, including anticancer and anti-HIV therapies, drugs for neurodegenerative diseases, drug delivery systems, and preparations that retard aging. In particular, a group of hydrophilic $C_{60}$ derivatives, carboxyfullerenes, were proposed to increase metazoan's lifespan (U.S. Patent Application 2003/0162837). However, water-soluble fullerenes are difficult to synthesize and to purify. Besides, in contrast to pristine $C_{60}$, which is non-toxic, some $C_{60}$-derivatives can be highly toxic (Adv Exp Med Biol, 2007, 620, 168-80).

Pristine $C_{60}$ has been shown to be more effective as an antioxidant than certain carboxyfullerenes in Wang, I. et al., J. Med. Chem. 1999, 42, 4614-4620. However, $C_{60}$ has not been employed as an active ingredient to develop an in vivo treating method in this publication. Aqueous suspensions of $C_{60}$ are well known in the art. They are stable for long periods and can be delivered to cells. A study of 14C-labeled C-60 reported that it is possible to form suspensions of $C_{60}$ in water that are stable for long periods (J. Am. Chem. Soc. 1994, 116, 4517-4518). However, the authors failed to detect the fullerene inside the cells and these suspensions containing very low concentrations of fullerene (typically 0.1 mg per ml) were inadequate to perform in vivo studies, especially toxicity studies, and metabolic fate investigations ((J. Am. Chem. Soc. 1994, 116, 4517-4518). Other vectorisation methods include the formation of inclusion complexes with cyclodextrins, calixarenes, tween-20, micelles, liposomes, and vesicles; however the $C_{60}$ concentrations reached by such methods are still very low (1 mg/mL at most) and inadequate to perform in vivo toxicity studies. Further, these methods present another drawback because they generally necessitate a preliminary dissolution step of the fullerene in an organic solvent. Other studies proposed the use of $C_{60}$ nanoparticles suspended in aqueous media to form a colloidal solution so-called nC60, however such solutions proved to be highly toxic because they contain impurities linked to the oxidation byproducts of the solvents used during their preparation (Adv Exp Med Biol, 2007, 620, 168-80. Journal of Nanoscience Letters 2011, 1: 62-63). Another method, disclosed in J. Med. Chem. 2000, 43, 3186-3188 uses polyvinyl-pyrrolidone to solubilize $C_{60}$; however this vehicle can react with fullerene and the formed complex may cause harmful effects on mice embryos.

Moussa et al. described in Fullerene Science & Technology 1995, 3, 333-342 that partially micronized C6o particles can be incorporated into living human phagocyte cells. C6o was directly suspended in the culture media and did not exhibit acute toxicity. Moussa et al. also described in Fullerene Science & Technology 1996, 4, 21-29 that micronized particles of water-insoluble fullerenes may be administered to mice on the form of a biocompatible aqueous suspension comprising a surfactant (tween 80) and a suspending agent (carboxymethyl cellulose) which stabilizes the suspension. The authors disclosed that C6o is non-toxic, can cross cellular membranes and accumulates in liver and spleen (Fullerene Science & Technology 1996, 4: 21-29). The same group headed by F. Mousse have already used Micronized Ceo suspensions as free radical scavenger in vivo (Nano Letters 2005, 5: 2578-2585). However, the effective doses were very high (i.e. >1 g/kg of body-weight) and intra peritoneal (i. p.) administration was the only route of administration for such suspensions. The authors also disclosed that Ceo can solubilize in vivo inside lipid droplets (Nano Letters 2005, 5: 2578-2585). This result has been confirmed in vitro by other authors whom studied Oβo solubility in vegetable oils (Fullerenes, Nanotubes, and Carbon Nanostructures, 2007, 15: 311-314. Fullerenes, Nanotubes, and Carbon Nanostructures, 2007, 15: 331-339). Stable biocompatible compositions comprising water insoluble fullerenes dispersed and/or dissolved in a carrier selected from the group consisting of fats and oils in an amount ranging from 0.2 to 10% by weight relative to the total weight of the composition, preferably from 0.1 to 2% by weight, were already proposed by N Gharbi and F Moussa for preventing damages caused by free radicals (2005/International Application No. PCT/EP2005/004963). However, in such compositions the water-insoluble fullerene is not fully dissolved and their oral absorption was unknown. Further, large aggregates of the administered fullerene can be filtered by liver and spleen and confined in their reticulo-endothelial system (RES) thus altering the diffusion and biodistribution of Ceo in the whole body. Thus, the in vivo use of water-insoluble fullerenes as free radical scavengers through delivery thanks to a non-aqueous carrier is still not satisfactory.

The inventors of the instant invention have now discovered a surprising use of [60]fullerene as agent that promotes an increases in the overall length of the expected lifespan of mammals.

Compositions comprising [60]fullerene and their use for preventing damages caused to metazons by free radicals are disclosed in TN Patent No. TN 2011/327 issued Jun. 30, 2011 to Moussa et al. which is incorporated herein by reference in its entirety.

SUMMARY OF THE INVENTION

It is in view of the above problems that the present invention was developed. The main objective of the invention is to provide a process or method for extending the longevity of a mammal, which comprises a step of administering to said mammal a composition comprising an effective amount of [60]fullerene, which avoids the drawbacks of the prior art processes, and in particular: 1—avoids the use of charge transfer complexes, 2—avoids the use of organic solvents, and 3—avoids in situ aggregation of the administered fullerene. It has now been discovered by the inventors that the compositions comprising [60]fullerene dissolved in a suitable carrier selected from the group consisting of oils and fats proved suitable to achieve the aforementioned objectives. In particular, not only they allow [60]fullerene to be administered orally or intramuscularly or intra peritoneally to prolong the longevity of mammals but they are at least several times more active than previous compositions. Thus, a first embodiment of the instant invention comprises a stable biocompatible composition comprising (a) a carrier selected from the group consisting of fats and oils; and (b) [60]fullerene, wherein [60]fullerene is almost dissolved in said carrier. The embodiment is further drawn to compositions, in which [60]fullerene is dissolved in the carrier. Another embodiment of the instant invention is a method to prolong the longevity of mammals, which comprises a step of administering to said mammal a stable biocompatible composition comprising an effective amount of [60]fullerene dissolved in a carrier selected from the group consisting of fats and oils. In a preferred embodiment, the invention is drawn to a method of prolonging the longevity of mammals, which comprises a step of adding to food or any nutritional composition a stable composition comprising an effective amount of [60]fullerene dispersed in a carrier selected from the group consisting of fats and oils.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The foregoing and other objects, features and advantages of the present invention will become readily apparent to those skilled in the art from a reading of the detailed description hereafter when considered in conjunction with the accompanying drawings wherein.

DETAILED DESCRIPTION OF THE INVENTION AND PREFERRED EMBODIMENTS

Free radicals are constantly formed in vivo. Some of these molecules are physiologically useful, but they can also result in pathological oxidative stress to cells and tissues. Endogenous defences include both antioxidants and repairing systems. However, excess production of free radicals, their production in inappropriate relative amounts or deficiencies in endogenous defences can have deleterious effects. Free radicals can cause oxidative damage to lipids, DNA, bio molecules, rises in the concentration of intracellular calcium, as well as activation of proteases, nucleases and protein kinases. Considerable evidence supports the view that oxidative damage involving free radicals occurs in most, if not all, human diseases. Oxidative stress is now recognized as an important contributor to the development of many human diseases including liver fibrosis, ischemia-reperfusion, atherosclerosis, several neurological disorders and age-related cancer as well as to process of ageing. Thus antioxidants and systems that can protect against oxidative stress are needed to maintain health and prolong the expected lifespan in metazoans. This has led to attempts to develop additional antioxidants to supplement the antioxidant defences of cells as potential therapeutic agents. Diet-derived antioxidants and a number of small molecules that can scavenge free radicals as well as super oxide dismutase-mimetics and chelators of transition metal ions were proposed as potential therapeutic agents against oxidative stress. Compositions according to the invention comprising [60]fullerene have been found to exhibit highly efficient antioxidant properties in vivo. The fullerene core, i.e. the fullerene skeleton without lateral substituents, used in the practice of this invention comprise clustered carbon structures generally spherical in shape and having a carbon content of 60 carbon atoms. Typically, [60]fullerene according to the invention is present in an amount ranging from 0.01 to 0.0.08% by weight relative to the total weight of the composition, preferably 0.08% by weight. [60]fullerene is preferably dissolved in the carrier, i.e. the composition can be filtered through a 0.2 pm filter. The stable, biocompatible compositions according to the invention comprise a carrier selected from the group consisting of fats and oils; and [60]fullerene, wherein said fullerene is mostly dissolved in said carrier. The carrier used in the present invention is a pharmaceutically acceptable and biocompatible carrier, selected from the group consisting of fats and oils. The fat or oil may be any natural or synthetic fat or oil suitable for administration to a mammal. They are not particularly restricted inasmuch as they are components which can be used in pharmaceutical preparations or in foods. Oils and fats can be hydrogenated or partially hydrogenated. They are used at a solid, a semisolid, or a liquid state. Vegetable and animal fats and oils are preferred, vegetable fats and oils are most preferred. Oils and fats include, without limitation fatty acid esters, fatty acids, fatty alcohols and fatty alcohol esters. Synthetic lipids can also be used. Fatty acids, as defined herein, are intended to mean aliphatic monocarboxylic acids having a chain of 4 to 40 carbon atoms, which may be branched or unbranched, saturated or unsaturated, cyclic or acyclic. Fatty acids may be natural or synthetic, polyunsaturated, mono-unsaturated or saturated. Natural fatty acids, which are usually unbranched and C4-C28 even-numbered, are preferred. Examples of fatty acids include, but are not limited to, linoleic acid, arachidonic acid, linolenic acid, gamma-linolenic acid, caprylic acid, stearic acid, myristic acid, a palmitic acid, behenic acid, undecylenic acid, oleic acid, an decosahexaenoic acid (DHA), eicosapentaenoic acid (EPA), isostearic acid, 12-hydroxy-stearic acid. Salts thereof [e.g. alkali metal salts (sodium salts, potassium salts, etc.), alkaline earth metal salts (calcium, magnesium salts etc.)] can also be employed. Fatty acid esters are preferably esters of fatty acid as defined hereinabove with C-1-C40 aliphatic or aromatic alcohols, preferably aliphatic, saturated or unsaturated, straight-chain or branched-chain, cyclic or acyclic. Alcohols can be polyols, having preferably up to five hydroxyl groups. Examples of fatty acid esters include, but are not limited to, triglycerides i.e. tri-esters of glycerol with fatty acids cited above, sterids i.e. esters of sterols with fatty acids cited above, the group consisting of the lower alkyl esters thereof (preferably methyl, propyl, butyl, isopropyl and hexyl), 1,2- or 1,3-diglycerides, 1- or 2-monoglycerides, polyglycolysed glycerides such as sucrose fatty acid esters, polyglyceryl fatty acid esters, propylene glycol fatty acid esters. Specific examples of fatty acid esters are octyldodecyl behenate; isocetyl behenate; isocetyl lactate; isostearyl lactate; linoleyl lactate; oleyl lactate; isostearyl octanoate, isocetyl octanoate, decyl oleate, isocetyl isotearate, isocetyl laurate; isocetyl stearate; isodecyl octanoate; isodecyl oleate; isononyl isononanoate; isostearyl palmitate; myristyl isostearate; octyl isononanoate; 2-ethylhexyl isononanoate; octyl isostearate; octyldodecyl erucate; isopropyl palmitates, 2-ethylhexyl palmitate, 2-octyldecyl palmitate, branched alkyl myristates such as isopropyl myristate, t-butyl myristate, 2-octyldodecyl myristate, hexyl isostearate, butyl isostearate, isobutyl stearate, hexyl laurate, 2-hexyldecyl laurate, propylene glycol monostearate and distearate. Examples of glycerides (fatty acid esters) include, without limitation, triolein, trilinolein, tripalmitin, tristearin, trimyristin, and triarachidonin. Examples of sterids (fatty acid esters) include, without limitation, cholesteryl oleate, cholesteryl linoleate, cholesteryl myristate, cholesteryl palmitate, cholesteryl arachidate. Examples of fatty alcohols include, without limitation, cetyl alcohol, stearyl alcohol, lauryl alcohol, myristyl alcohol, palmityl alcohol, behenyl alcohol, hexadecyl alcohol, oleic alcohol, isostearyl alcohol, cetostearyl alcohol. They can be used as esters with C4-C40 dicarboxylic, tricarboxylic or tetracarboxylic acids. Oils may be natural oils such as vegetable oils and animal oils (composed predominantly of triglycerides), or mineral oils such as silicon oils, fluorinated oils. Liquid paraffin can also be used. Examples of natural oil include, but are not limited to, oils from plant sources, such as corn oil, wheat germ oil, soybean oil, rice bran oil, rapeseed oil, canola oil, sesame oil, palm (kernel) oil, olive oil, camellia oil, peanut oil, coconut oil, sunflower oil, peanut oil, orange oil, evening primrose oil, borage oil, blackcurrant seed oil, cottonseed oil, beaver oil, pineapple oil, safflower oil, copra oil, oils found in coffee, and animal oils such as turtle oil, fish oil, cod-liver oil. Fats may be mineral fats or natural fats such as vegetable fats and animal fats. Petrolatum, paraffin can also be used. Examples of natural fat include, but are not limited to, butter, cocoa butter, theobroma, peanut butter, lard, beef fat, chicken fat, horse fat, lanolin and lanolin derivatives.

Figure 1:
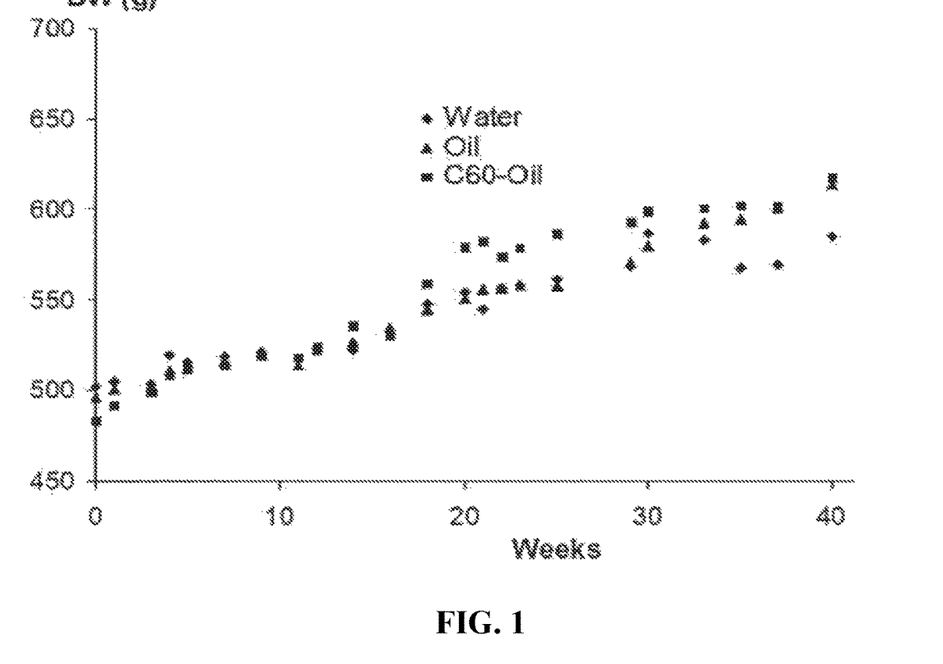
FIG. 1 is a representation of the growth rate of rats as a function of time, which were treated or not with a composition according to the present invention. Specifically, growth of surviving rats were treated with gavages (daily during one week, the weekly until the end of the second month then every two weeks until the end of the 7$^{th}$ month) of 1 ml of water or olive oil or $C_{60}$ dissolved in olive oil (0.8 mg/ml) (BW=body weight).
Figure 2:
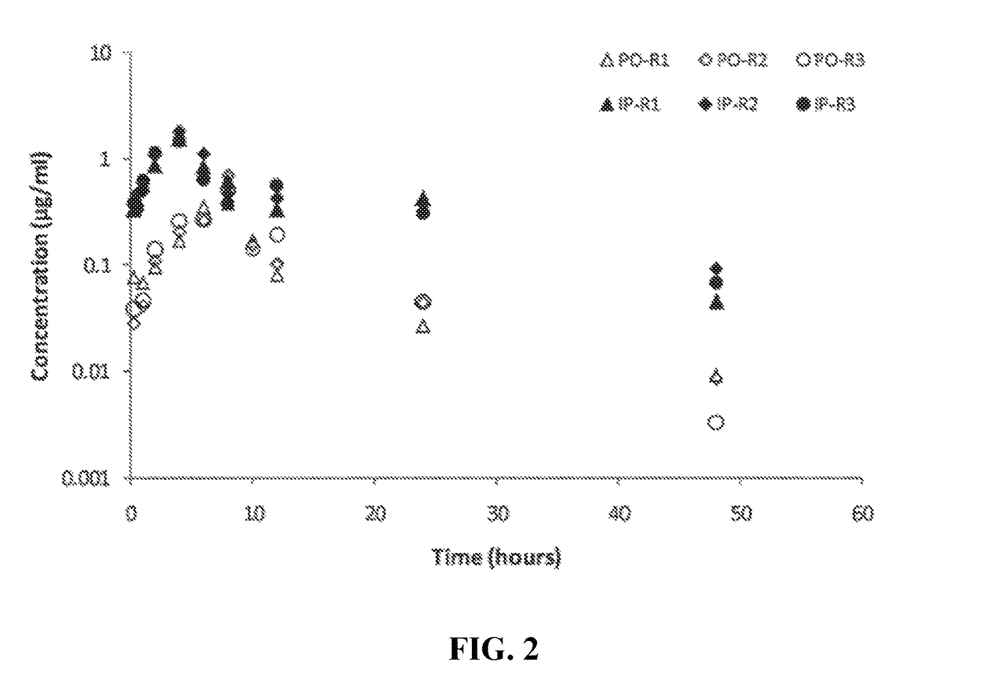
FIG. 2 shows whole blood Ceo concentrations-time plot (mean±S.E.) following single dose oral administration (4 mg/kg, n=3) or single dose intra-peritoneal (ip) bolus injection of the same dose (n=3) of Ceo dissolved in olive oil (0.8 mg/ml) (n=3) (R1, R2, R3=rat 1, rat 2 and rat 3)
Figure 3:
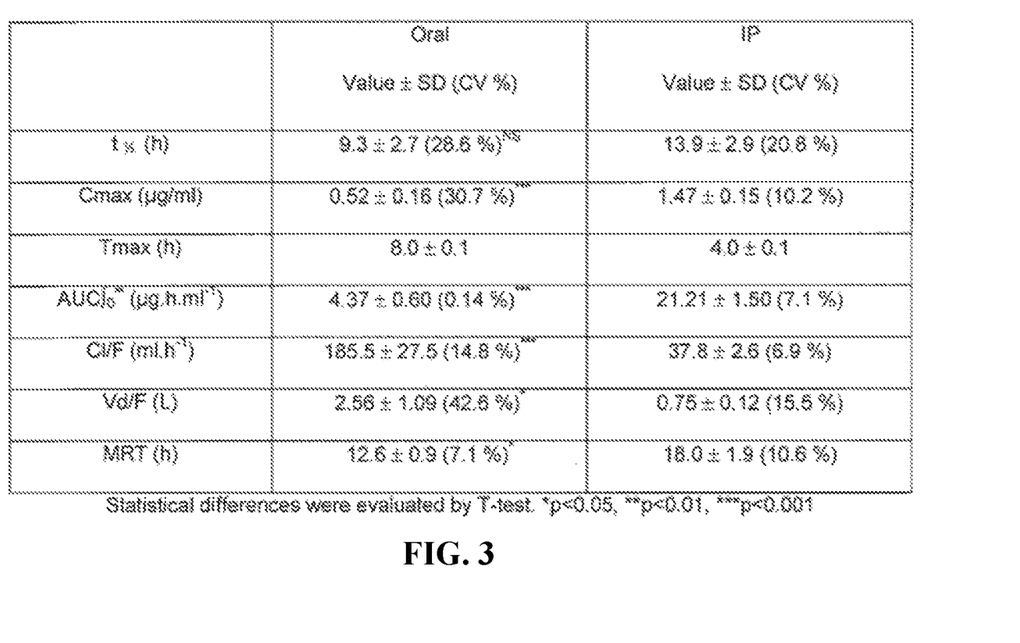
FIG. 3 illustrates Table 1 which provides mean pharmacokinetic parameters obtaine din rats after oral (n=3) or intra-peritoneal (n=3) administration of $C_{60}$ dissolved in olive oil.
Figure 4:
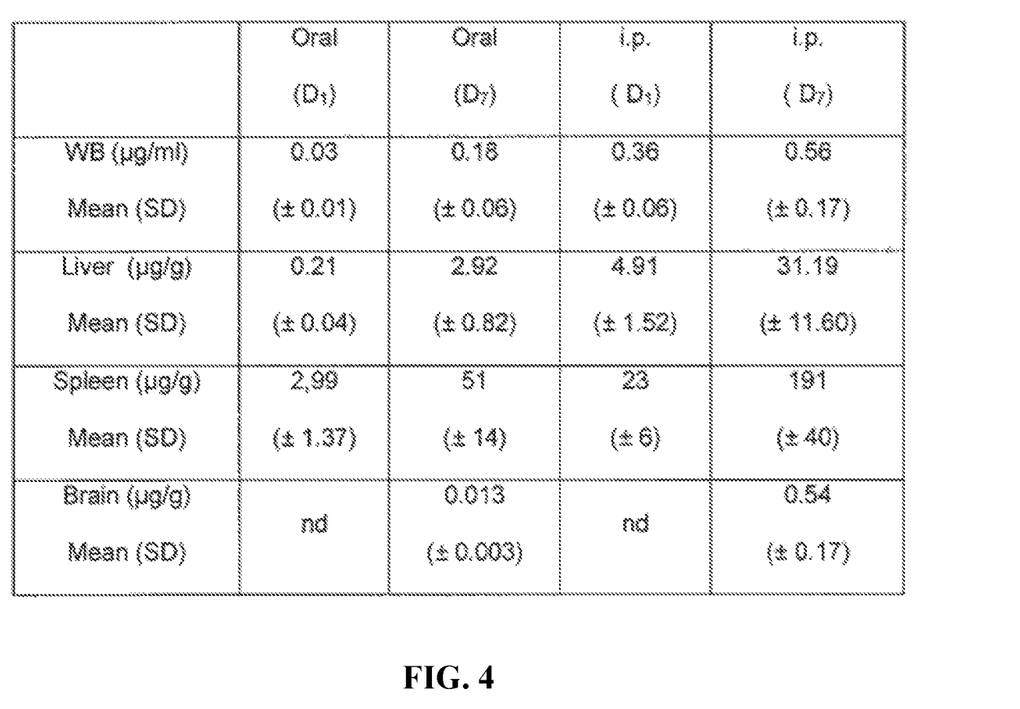
FIG. 4 illustrates Table 3 which provide $C_{60}$ concentration in whole blood (WB), liver, spleen and brain of rats daily treated with a single dose of $C_{60}$ dissolve din olive oil (4 mg/kg body weight) by oral (n=3) or i.p. route (n=3) (nd=not determined)

Oils and fats can be polyunsaturated such as corn, soybean, safflower oils, or saturated, such as palm, coconut oils and butter, or mono-unsaturated, such as olive oil and canola oil. Other suitable carriers according to the invention are diisopropyl sebacate; diisopropyl adipate; diisostearyl adipate; octyldodecyl stearoyl stearate; pentaerythrityl tetraisononanoate; pentaerythrityl tetraisostearate; triisopropyl citrate; triisostearyl citrate; and trioctyldodecyl citrate. Preferred carriers according to the invention are butter, cocoa butter, peanut butter, olive oil, soybean oil, cod-liver oil and liquid paraffin. As defined above, carriers may be used each alone or in a combination of two or more species. [60]fullerene is dissolved in the carrier, depending on the nature of the carrier. Some carriers are able to dissolve substantial amounts of water-insoluble fullerenes (several mg/g of carrier). In one embodiment, at least 0.8 mg of fullerene is dissolved per ml of the carrier (the carrier being a liquid). As an example, it is possible to dissolve a total weight up to 1 mg of C60 per g of olive or soybean oil in less than one week. The compositions according to the invention may be pharmaceutical compositions comprising the fullerene in a therapeutically effective amount. Preferably, said fullerene can protect against biologically reactive radical species, which means chemicals that are free radicals or contribute to the generation of free radicals. Generally, the biologically reactive radical species are generated from O2 or H2O2. Thus, the invention also concerns a method to prolong the longevity of a mammal, which comprises a step of administering to said mammal a stable biocompatible composition as defined hereinabove. [60]fullerene, when dissolved in the carriers of the present invention, can be administered to mammals and this compound is well absorbed by said mammals. Generally, the said fullerene is administered in an amount of at least 0.1 mg/kg of body weight per day. According to the method of the invention, the inventive compositions may be administered orally, intramuscularly, subcutaneously, intra dermally or intra peritoneally, rectally by suppositories or sublingually. For oral ingestion by a mammal to be treated, the carrier is preferably an edible carrier. In at least one embodiment, said composition is administered in a pure form. In another embodiment, it is administered in the form of an emulsion in water. In another embodiment the fullerene is administered as a labile C6o-derivative derivative that can deliver Ceo after administration. The compositions of the instant invention can be in any liquid or solid conventional pharmaceutical formulation. The carrier enables the fullerene to be formulated as tablets, pills, dragees, capsules, liposome, pomade, ointment, cream, lotion, emulsions, gels, syrups, slurries and the like. The compositions of the present invention are preferably presented for oral administration to mammals in unit dosage forms, such as tablets, capsules, and oral solutions, containing suitable quantities of [60]fullerene. The compositions may be sterilized and/or may contain some adjuvants such as preservatives, stabilizers, acidity regulators, natural or synthetic flavour, anti-foaming agents, viscosity-control agents, emulsifiers, salts for varying the osmotic pressure and/or other buffers. In addition, compositions may contain other pharmaceutically active agents. The level of free radicals and reactive oxygen species in mammal cells decreases following treatment as compared to the level of reactive oxygen species in a cell that has not been contacted with a composition according to the invention. Indeed, [60]fullerene according to the invention can act as antioxidant and supplement the antioxidant defences of cells. That means they inhibit oxidation or inhibit reactions promoted by reactive oxygen species. Physiologically relevant reactive oxygen species, which contribute to the generation of free radicals, include hydrogen peroxide, super oxide anion, and the like. The protective method of the invention reduces cell damage and death, and thus generally maintains the health of treated mammals. Further, the inventors discovered that [60]fullerene administered as biocompatible composition as described herein—1) can be absorbed after oral administration (FIG. 2); —2) they can react inside the liver with vitamin A (retinol) and esters thereof following a Diels-Alder-like reaction without any toxic effect (New J Chem, 1998, 989-992); —3) they are eliminated through the bile ducts (Nano Letters 2005, 5 (12): 2578-2585); and—4) despite the large amounts administered, no acute or sub-acute toxicity could be observed in mice and rats. No behaviour or growth disorder could be observed in treated animals either, which can be seen on FIG. 1. The latter shows growth rate of three groups (n=6) of rats which received weekly per os 1 ml of olive oil containing 0.8 mg of Ceo or 1 ml of olive oil only or 1 ml of water only. The in vivo new properties of [60]fullerene are due to fullerenes themselves and/or to the fullerene-retinol and fullerene-retinyl ester adducts formed after administration inside the liver. Also disclosed herein is a method for preparing a composition according to the present invention, comprising a carrier and particles of [60]fullerene. Said method comprises the steps of: —(a) Charging a milling vessel with the fullerene, the carrier and balls, said milling vessel and balls being made out of any biocompatible metal or polymer; —(b) Agitating the mixture resulting from step (a) until a homogeneous dissolution is obtained; and—(c) Sterilizing the composition resulting from step (b) by filtration. Direct mechanical milling in the carrier presents the advantages to accelerate the dissolution. Said method comprises the steps of: —(a) Charging a milling vessel with the fullerene, the fat or oil and balls, said milling vessel and balls being made out of any biocompatible metal or polymer; —(b) Agitating the mixture resulting from step (a) until complete homogenization of the solution; —(c) Agitating the composition resulting from step (b) until complete dissolution of the fullerene; and—(d) Sterilizing by filtration the composition resulting from step (c). Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches. Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. The invention is further illustrated by the examples described below. These examples are meant to illustrate the invention and are not to be interpreted as limiting the scope of the invention.

EXAMPLES

General Considerations

C60 (Purity: 99.98%) was purchased from Term USA (Fort Bragg, Calif., USA). Its characterization and its purity were assessed by HPLC, UV, C-NMR, and Mass Spectrometry. No impurity could be observed. It was used without further purification as well as after sublimation. All the other reagents were analytical grade and were purchased from Sigma (St Louis, Mo.). Animals received human care and the study protocols complied with general guidelines for the care and use of laboratory animals. Male Wistar rats (Charles River, France) were housed by groups of 3 in polypropylene cages at constant temperature (22° C.) and humidity (60%) and with a 12 h light/dark cycle, and fed a standard diet ad libitum. All rats were allowed to acclimate to this facility for at least one week before being used in the experiments. At the end of the experiment, body weights were determined and the animals were sacrificed under the same conditions by bleeding through the thoracic aorta after sodium pentobarbital (1.0 mL/kg of body weight) anaesthesia.

Biochemical tests, Cso determinations and statistics were processed as previously described in Nano Letters 2005, 5 (12): 2578-2585.

Example 1

Direct Dissolution of [60]Fullerene in a Vegetable Oil

In the stainless steel milling vessels of a Pulverisette 7 (Fritsch, Idar-Oberstein, Germany) or a similar device, add 8 mg of [60]fullerene and 10 mL of olive oil or 10 g of butter and 6 stainless steel balls (8 mm of diameter) (the milling vessels and the balls can be made out of any biocompatible metal or polymer such as stainless steel, tempered chrome steel, silicon nitride, corundum, tungsten carbide, agate, oxide of zirconium etc). Agitate the mixture during several hours (at 600 rpm for instance) until complete dissolution. The resulting homogenous solution or paste is then ready for use for oral administration or by any route of administration after appropriate sterilization. Sterilization may be achieved by filtration under vacuum (pore size: 0.2 μηι). The sterilized composition is stable for at least 1 month. It is also possible to dissolve water-insoluble fullerenes in natural or mineral oils without stirring however the dissolution may be time consuming (up to several days at room temperature). Therefore, the former protocol is preferred. The fullerene concentration in compositions according to the invention can be determined by HPLC after adequate dilution in mobile phase as described previously (J. Chromatogr. B 1997, 696: 153-159).

Example 2

Pharmacokinetics and Biodistribution of an Oily Solution after Oral and Intra-Peritoneal Administration in Rats Pharmacokinetic studies were carried out with male Wistar rats (weighing 200-220 g). Rats were housed in individual cages and maintained in an air-conditioned room (22-25° C.) on a 12 h light/dark cycle with water and food available. The rats were acclimated for 7 days and they were fasted overnight but with access to water, before treatment.

Under general anesthesia, a catheter was introduced into the rat right jugular vein, positioned subcutaneously with the tip in the inter-scapular region. The prepared rats were then allowed to recover for 24 h, and the blood catheters were flushed with 0.9% NaCl solution containing 20 I U/ml of heparin to avoid possible clot obstruction. Before Ceo administration, the rats were fasted overnight but with access to water. The same single dose of Ceo (4 mg/kg) was delivered orally, by a gavages needle, or intra-peritoneally to two groups of three rats. Blood (0.20 ml) was withdrawn via the canular prior to dosing (f=0) and at 15, 30, 60 min and then at 2, 4, 8, 10, 12, 24 and 48 h post-dosing. Antithrombin heparin (20 IU/ml) was added in each blood sample. After each blood collection 0.20 ml of sterile 0.9% NaCl solution were injected to the animal, to avoid hypovolemia. The rats were sacrificed 48 h after eo administration for organ collection (livers, spleens, and brains).

It was now discovered by the inventors that:—1) Soluble Ceo is absorbed and eliminated after either intraperitoneal or oral administrations. Table 1 represents the main pharmacokinetic parameters; 2—the maximal concentrations (Cmax) are reached 4 and 8 hours after i.p. and oral administrations, respectively (FIG. 2); 3—the maximal concentration after i.p. administration (1.47±0.15 pg/ml) is higher than that after oral administration (0.52±0.16 Mg/ml). Consequently, the area under the curve (AUC) is about 5 times larger when Ceo is administered by i.p. route as compared to oral route. Although these results do not allow determining the bioavailability of Ceo, they clearly show that a non-negligible % of the orally administered dose is absorbed as compared to the i.p. administered one (FIG. 2); and—3) the fullerene is well distributed in the whole body, in particular it can cross the brain barrier (table 2).

Example 3

Ceo-Induced Protection of the Liver against Acute Toxicity of Carbon Tetrachloride (CCU) in Rats Carbon tetrachloride is a classical hepatotoxicant that causes rapid liver damage progressing from steatosis to centrilobular necrosis. CCU intoxication in rodents is an important model far elucidation of the mechanism of action of hepatotoxic effects such as fatty degeneration, fibrosis, hepatocellular death, and carcinogenicity. These effects are consistent with the known induced metabolic activation of CCl4 to reactive intermediates, including CCl3" and CCl02' free radicals, and mobilization of intracellular calcium. Kupffer cells (liver resident macrophages) participate in the mechanism of toxicity of CCl4 in vivo by release of chemoattractants for neutrophils and a series of chemical mediators (cytokines). Both expression and synthesis of these cytokines are mainly modulated through redox-sensitive reactions. Further, involvement of reactive oxygen species and lipid peroxydation products can be demonstrated in other fundamental events of hepatic fibrogenosis, like activation of hepatic stellate cells (HSC: liver resident nonparenchymal cells also referred to as fat-storing or perisinusoidal cells, lipocytes and Ito cells). In a previous work, the effects of C60-pretreatments on acute carbon tetrachloride intoxication in rats, a classical model for studying free-radical-mediated liver injury was reported. The results obtained by the authors leaded by F Moussa (Nano Letters 2005, 5 (12), 2578-2585) showed that aqueous C6o suspensions not only have no acute or subacute toxicity in rodents but they also protect their livers in a dose-dependent manner against free-radical damage. The most effective dose of C6o reported in the latter paper was about 2.5 g/kg of body-weight and was administered intra-peritoneally and the better protection was obtained at day 14 after administration. It was now discovered by the inventors that the fullerene is about 100 times more active it is administered in solution than in suspension, and the effect is more rapid (24 hours after administration) as compared to the results published previously in the same experimental model (Nano Letters 2005, 5: 2578-2585).

Example 4

Ceo Prolongs the Longevity in Rats without Chronic Toxicity

The rats were housed one per cage and acclimated for 14 days, before dosing. Three groups of 10 rats (10 months old, weighing 495±31 g) were administered daily for one week, then weekly until the end of the second month and then every two weeks until the end of the 7th month, by gavages with 1 ml of water or olive oil or Ceo dissolved in olive oil (0.8 mg/ml), respectively. The rats were weighed before each dosing. Routine observations following official recommendations (EC Commission Directive 2004/73/EC of 29 Apr. 2004 Adapting to Technical Progress for the Twenty-Ninth Time Council Directive 67/548/EEC on the Approximation of the Laws, Regulations and Administrative Provisions Relating to the Classification, Packaging and Labeling of Dangerous Substances. O.J. No. L1522004) were made on all animals inside and outside the cage once a day throughout the study for signs of departure from normal activity, morbidity and mortality.

Figure 5:
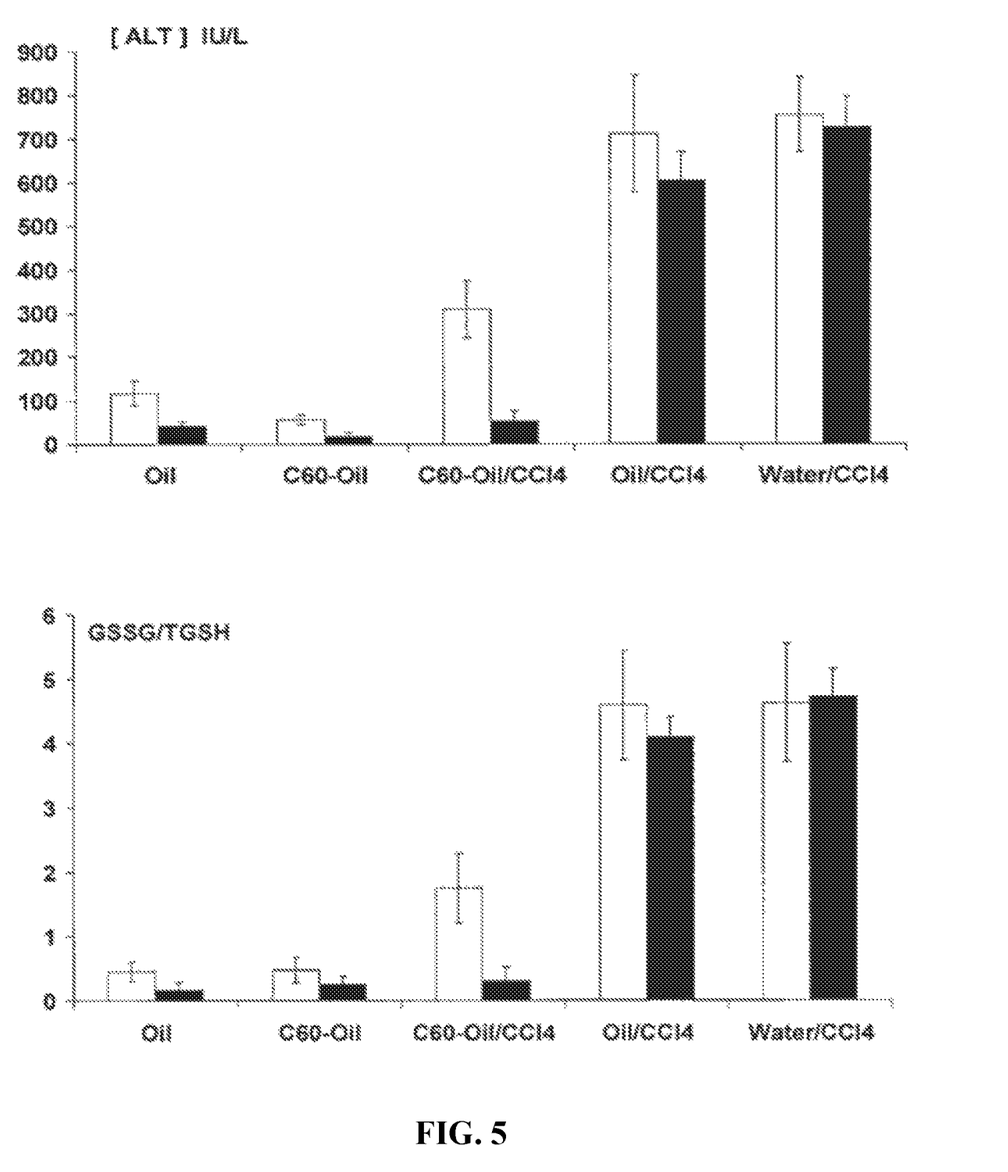
FIGS. 5 and 6 show the results of some biochemical tests for Ceo pre-treated and control rats before CCl4 administration.
Figure 6:
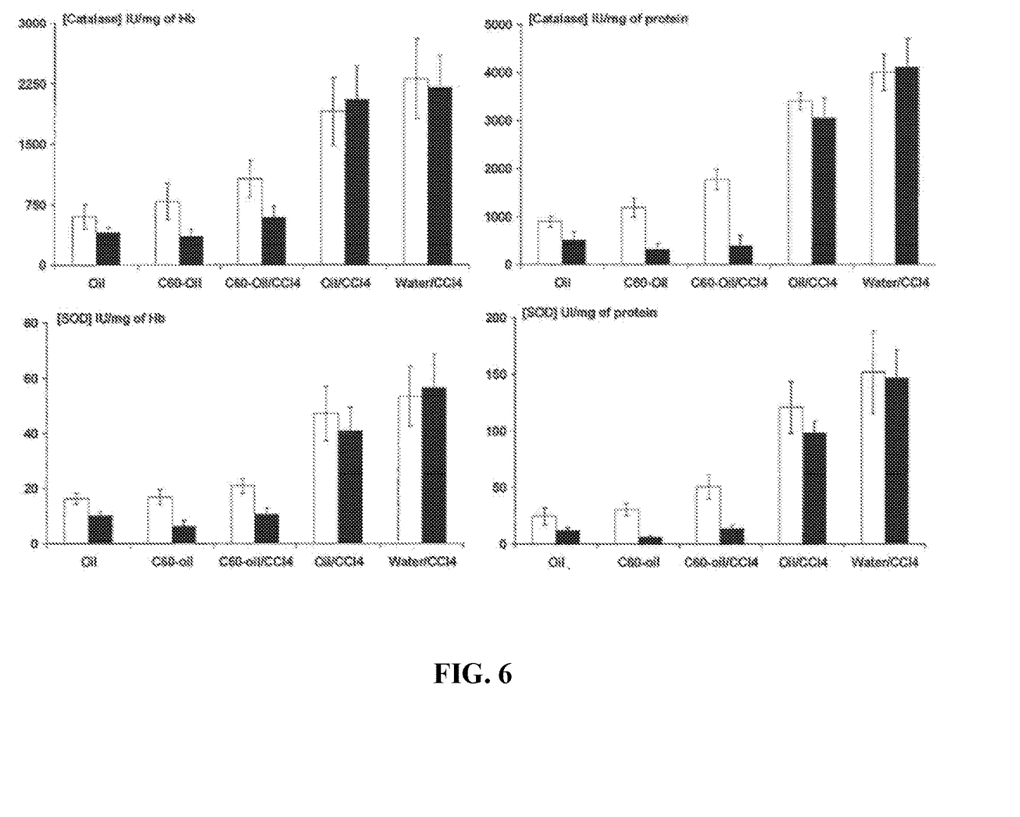
Figure 7:
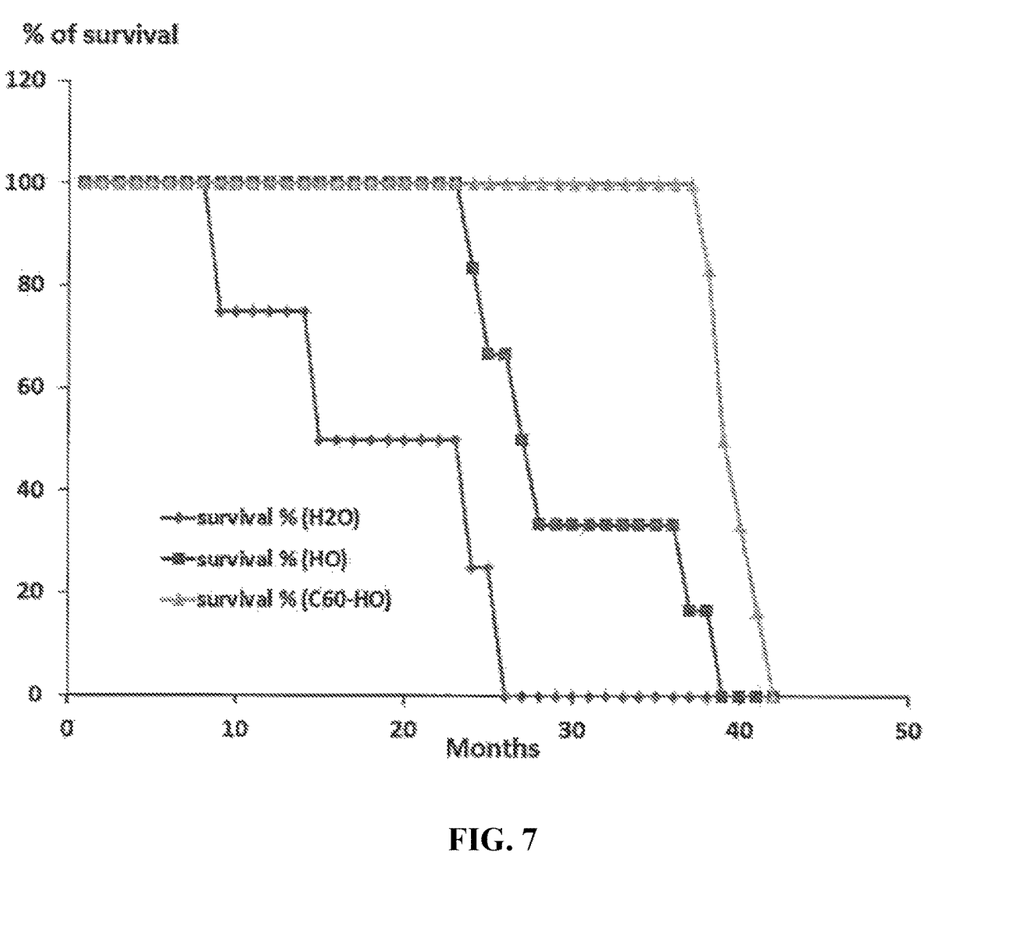
FIG. 7 represents the survival percentage of rats (n=6 per group) orally treated with Ceo at the age of 10 months (1 ml/kg of body-weight, weekly until the end of the second month then every two weeks until the end of the 7th month, with water, olive oil or Ceo dissolved in olive oil (0.8 mg/ml)). Table 1 summarizes the mean pharmacokinetic parameters obtained in rats after oral (n=3) or intra-peritoneal (n=3) administration of Ceo dissolved in olive oil and table 2 summarizes Ceo concentrations in whole blood (WB), liver, spleen and brain of rats daily treated with a single dose of Ceo dissolved in olive oil (4 mg/kg body weight) by oral (n=3) or ip route (n=3).

This experiment was initiated after observing that Ceo is absorbed through oral administration. To study the chronic toxicity of Ceo we designed a protocol according to the general guidelines of US food and drug administration (Chronic Toxicity Studies with Rodents in Toxicological Principles for the Safety Assessment of Food Ingredients. Redbook 2000, revised July 2007, Chapter IV.C.5.a. IV.C.5.a.) with some modifications. It was now discovered by the inventors that oral administration of Ceo increases significantly the longevity of rats (FIG. 5). At 25 months after the beginning of the treatment, the % of survival is equal to 25%, 67% and 100% for the rats treated with water, olive oil or C6o-dissolved in olive oil, respectively (FIG. 5). At 37 months, after the beginning of the treatment, this percentage is always equal to 100% for the rats treated with C6o-dissolved in olive oil, 17% for the rats treated with olive oil, and 0% for the rats treated with water (FIG. 5). The increase of the expected lifespan reported herein has never been reported for any other substance, to our knowledge.

What is claimed is:

1. A method of prolonging the lifespan of a mammal, comprising:
    orally administering to the mammal a homogenous solution consisting essentially of a water-insoluble $C_{60}$ fullerene dissolved in a olive oil,
wherein:
    the water-insoluble $C_{60}$ fullerene is present in the homogenous solution at a concentration of 0.08% by weight, relative to the total weight of the homogenous solution; and
    the homogeneous solution is administered such that the mammal receives a dosage of 1.6 milligrams of the water-insoluble $C_{60}$ fullerene per kilogram of body weight of the mammal.

2. The method of claim 1, wherein the composition is orally administered neat or as a dispersion in water.

3. The method of claim 1, wherein the composition further comprises food or a nutritional composition.

4. The method of claim 1, wherein the mammal is a human.

5. A method of prolonging the lifespan of a mammal, comprising:
    orally administering to the mammal a homogenous solution consisting of a water-insoluble $C_{60}$ fullerene dissolved in olive oil,
wherein:
    the water-insoluble $C_{60}$ fullerene is present in the homogenous solution at a concentration of 0.08% by weight, relative to the total weight of the homogenous solution,
    the composition is administered such that the mammal receives a dosage of 1.6 milligrams of the water-insoluble $C_{60}$ fullerene per kilogram of body weight of the mammal, and
    the homogenous solution is characterized as having been filtered through a 0.2 µm filter.

* * * * *

UNITED STATES PATENT AND TRADEMARK OFFICE
CERTIFICATE OF CORRECTION

PATENT NO. : 11,471,484 B2
APPLICATION NO. : 15/927703
DATED : October 18, 2022
INVENTOR(S) : Fathi Moussa It is certified that error appears in the above-identified patent and that said Letters Patent is hereby corrected as shown below:

On the Title Page

Item (12), delete "Moussa et al." and insert --Moussa--.

Item (72), please remove "Manef Abderrabba, Sidi Rezig-Megrine (TN)" from the list of inventors.

Signed and Sealed this
Twenty-eighth Day of February, 2023

Katherine Kelly Vidal
*Director of the United States Patent and Trademark Office*